(12) United States Patent
Forest

(10) Patent No.: US 8,741,888 B2
(45) Date of Patent: Jun. 3, 2014

(54) SLEEP AID COMPOSITION AND METHOD

(75) Inventor: Carl A. Forest, Boulder, CO (US)

(73) Assignee: Carl A. Forest, Boulder, CO (US)

( * ) Notice: Subject to any disclaimer, the term of this patent is extended or adjusted under 35 U.S.C. 154(b) by 84 days.

(21) Appl. No.: 13/145,072

(22) PCT Filed: Nov. 29, 2010

(86) PCT No.: PCT/US2010/058229
§ 371 (c)(1),
(2), (4) Date: Jul. 18, 2011

(87) PCT Pub. No.: WO2012/064349
PCT Pub. Date: May 18, 2012

(65) Prior Publication Data
US 2012/0214793 A1    Aug. 23, 2012

Related U.S. Application Data

(60) Provisional application No. 61/411,569, filed on Nov. 9, 2010.

(51) Int. Cl.
*A61K 31/554* (2006.01)
*A61K 31/415* (2006.01)

(52) U.S. Cl.
USPC ...................... 514/211.13; 514/393

(58) Field of Classification Search
USPC ............. 514/211.13, 393; 540/551; 544/58.4, 544/127, 262; 546/121
See application file for complete search history.

(56) References Cited

U.S. PATENT DOCUMENTS

| 4,382,938 | A | 5/1983 | Kaplan et al. | |
|---|---|---|---|---|
| 4,879,288 | A | 11/1989 | Warawa et al. | |
| 6,638,535 | B2 * | 10/2003 | Lemmens et al. | 424/489 |
| 7,820,695 | B2 * | 10/2010 | Weiner et al. | 514/317 |
| 2003/0180352 | A1 * | 9/2003 | Patel et al. | 424/465 |
| 2005/0233010 | A1 | 10/2005 | Satow | |
| 2008/0064671 | A1 | 3/2008 | Barlow et al. | |
| 2008/0103105 | A1 | 5/2008 | Barlow et al. | |
| 2008/0103165 | A1 | 5/2008 | Barlow et al. | |
| 2008/0108574 | A1 | 5/2008 | Barlow et al. | |
| 2008/0167291 | A1 | 7/2008 | Barlow et al. | |
| 2009/0035370 | A1 | 2/2009 | Bortz et al. | |
| 2011/0071080 | A1 * | 3/2011 | Mates et al. | 514/11.4 |

OTHER PUBLICATIONS

Mariani et al., "Quetiapine Treatment of Zolpidem Dependence"; 2007, Am J Addict.; 16(5): 426.*
"Anyone Else Taking Seroquel Plus Ambien for Sleep?" *The Depression Forums*, Jun. 3, 2009.
"Quetiapine: Adverse Effects," *Wikipedia*. Jul. 19, 2011.
"Seroquel with Haldol or Ambien CR," *Alzheimer's Association Online Community*, Message Boards Forum, Questions for the Care Consultant, Sep. 17, 2008.
"Sleeping Aid Composition," *Cardinal Search Report*, 2010; pp. 1-8.
Breggin, P.R., "Brain damage, dementia and persistent cognitive dysfunction associated with neuroleptic drugs. Evidence, etiology, implications," *Journal of Mind and Behavior*, 1990; 11:426-464.
International Search Report and Written Opinion in co-pending PCT Application No. PCT/US10/58229 dated Feb. 2, 2011.
Kirkwood, C.K., "Management of Insomnia," *J. Am. Pharm. Assoc.*, 1999; 39(5):688-696 (Abstract).
Mariani et al., "Quetiapine Treatment of Zolpidem Dependence," *American Journal in Addictions*, 2007; 16(5):426.
Rosenberg, R.P., "Sleep maintenance insomnia: strengths and weaknesses of current pharmacologic therapies," *Ann Clin Psychiatry*, 2006; 18(1):49-56 (Abstract).
Treisman et al., "Insomnia," *Johns Hopkins POC-IT Center*, Jun. 12, 2010; (online) pp. 1-3.

* cited by examiner

*Primary Examiner* — My-Chau T Tran
(74) *Attorney, Agent, or Firm* — Patton Boggs LLP

(57) ABSTRACT

A sleep composition including zolpidem and quetiapine in combination provides a healthy sleep pattern allowing the user to get seven or eight hours sleep. The amount of each ingredient in the combination is lower than the amount usually needed to provide this amount of sleep when the ingredients are being used alone.

10 Claims, No Drawings

SLEEP AID COMPOSITION AND METHOD

CROSS-REFERENCES TO RELATED APPLICATIONS

This application is the National Stage of PCT Application No. PCT/US10/58229 filed Nov. 29, 2010, which claims the benefit of U.S. Provisional Application No. 61/411,569 filed Nov. 9, 2010, which applications are hereby incorporated by reference to the same extent as though fully contained herein.

BACKGROUND OF THE INVENTION

1. Field of the Invention

This invention relates in general to compositions and methods to assist humans in falling asleep and staying asleep for a normal period, and more particularly to such a composition that is consistently effective over long-term use at relatively low dosages and which has minimal side effects.

2. Background of the Invention

Sleep maladies such as insomnia are common in human beings, have serious consequences by themselves, and can lead to numerous other medical problems, even death. The consequences range from irritability, which destroys relationships and business through lowered performance and loss of the ability to function, to sickness associated with lowered resistance, such as pneumonia.

Inability to sleep is a complex phenomenon having causes as simple as the inability to put the day's events out of mind to changing metabolism and diet. Though it has been the subject of intensive study and research, it Is not yet fully understood.

The seriousness of sleep malfunction is such that innumerable remedies and methods have been created to deal with the problem. See Treisman et al., "Insomnia," *Johns Hopkins POC-IT Center,* 12 Jun. 2010 (online) pp. 1-3, which discusses insomnia treatment for HIV patients and gives recommendations for initial dosages of a variety of medications. Examples of sleep medications include over-the-counter medicines such as Tylenol PM®, compositions containing melatonin, herbal remedies, as well as pharmaceuticals such as zolpidem, quetiapine, and many others. It also includes sleep-inducing processes such as sleep-inducing music and videos. Sleep malfunction is so dehabiliting to those to whom it occurs that they often will blindly grab at any composition or process that promises relief. While some of these are effective, tolerance generally develops for most medications requiring increasingly higher dosages. There as yet does not exist a sleep assist composition or method that is effective, does not have significant undesirable side effects, and does not require increasingly higher dosages to remain effective. The very proliferation of sleep remedies is a testament to both the seriousness of the problem and the lack of a suitable solution to the problem.

Zolpidem, mentioned above, for some time was widely prescribed by physicians. However, like many other sleep medications, the body develops tolerance for the drug, and larger and larger dosages are required for it to remain effective. The tolerance can develop after just a few weeks of use. Moreover, zolpidem becomes addictive if taken for an extended period of time, i.e., about two months or longer, due to drug tolerance and physical dependence. C. K. Kirkwood, "Management of Insomnia", *J. Am. Pharm. Assoc.* (Wash) 1999 September-October: 39(5) 688-696; and Mariani et al., "Quetiapine Treatment of Zolpidem Dependence," *American Journal in Addictions,* 2007 (16 Apr. 2009-online), Vol. 16, Issue 5, p. 426. Sleep becomes impossible without it. Further, it is effective for only about four hours, after which the user usually wakes up. Thus, it is now available in an extended release formulation. However, the extended release formulation makes it difficult to wake up and function properly if there becomes a need to wake up after the medicine has been taken, such as the user's child that needs assistance or some other emergency. Further, it still has the problems that one becomes dependent on it for sleep and, as time goes on, ever larger doses are required for effectiveness. Other sleep medications can be substituted for zolpidem to break the dependence, but tolerance also develops for these substitutes. See Mariani et al., supra. Quetiapine is approved for psychic uses and is not approved for sale as a sleep medication, but physicians often prescribe it for sleep. In the Mariani et al. report, the development of tolerance for the quetiapine ultimately required dosages of 800 mg. Moreover, quetiapine does not enter the system for about an hour or more after being ingested. Thus, if the user forgets to take it until the user is ready to sleep, the result is an extended period of wakefulness. This wakefulness can lead to restlessness that prevents the drug from taking effect. While quetiapine tends to keep the user asleep longer than zolpidem, it still does not provide a full eight hours of sleep unless it is taken in a large enough dosage that creates drowsiness into the working day. In fact, the recommended amounts of quetiapine generally result in the side effect of somnolence (drowsiness). See Wikipedia, Quetiapine: Adverse Effects and astrazeneca-us.com at /pi/Seroquel.pdf at Adverse Reactions.

Zolpidem and quetiapine are both mentioned in a number of patent applications. See United States Published Patent Application No. US 2008/0064671 A1 (hereinafter "the '671 Application") published Mar. 13, 2008, in the names of Carrolee Barlow, Todd A. Carter, Andrew Morse, Kal Trenner, and Kym L. Lorrain and assigned to BrainCells, Inc.; United States Published Patent Application No. US 2008/0103165 A1 (hereinafter "the '165 Application") published May 1, 2008, in the names of the same inventors as the '671 Application and assigned to BrainCells, Inc.; United States Published Patent Application No. US 2008/0103105 A1 (hereinafter "the '105 Application") published May 1, 2008, in the names of the same inventors as the '671 Application and assigned to BrainCells, Inc.; United States Published Patent Application No. US 2008/0108574 A1 (hereinafter "the '574 Application") published May 8, 2008, in the names of the same inventors as the '671 Application and assigned to BrainCells, Inc.; United States Published Patent Application No. US 2008/0167291 A1 (hereinafter "the '291 Application") published Jul. 10, 2008, in the names of the same inventors as the '671 application and assigned to BrainCells, Inc. (all of the foregoing referred to together as "the BrainCells Applications"). The '671 Application discloses the use of a 4-acylaminopyridine derivative in combination with one or more other neurogenic agents for more than a hundred different human disorders which include sleep disorders (see [0082]). Several thousand different neurogenic agents are mentioned that can be used in combination with the 4-acylaminopyridine derivative. In some embodiments, a reported anti-psychotic agent is used in combination with the 4-acylaminopyridine derivative. One anti-psychotic agent mentioned is quetiapine ([0131]). In other embodiments, a GABA-A modulator is the neurogenic agent ([0203]). Many hundreds of possible GABA-A modulators are mentioned ([203]-[207]), including zolpidem ([0206]). The reference never mentions that quetiapine and zolpidem should be used together. The other BrainCells Applications all have essentially the same disclosure as the '671 application, except that the agent that is the key ingredient in the combinations is different. Again, quetiapine and zolpidem are mentioned only as one part of the disclosed combination in different ones of many thousands of possible embodiments; and it is never suggested that they be used together.

United States Published Patent Application No. US 2005/0233010 A1 (hereinafter "Satow") published Oct. 20, 2005, in the name of Phillip Maxwell Satow discloses a therapy that administers a lithium salt together with another pharmaceutically active agent (see [0026]). In certain embodiments, the lithium is co-administered with a sedative-hypnotic drug, one of which is zolpidem (see [0031]). In another aspect of the invention, a patient suffering from anxiety, depression, or a psychotic disorder is treated by co-administering lithium carbonate together with an atypical antipsychotic, one of which is quetiapine (see [0047]). It is not disclosed that zolpidem and quetiapine are combined.

United States Published Patent Application No. US 2009/0035370 (hereinafter "Bortz et al.") published Feb. 5, 2009, in the names of Jonathan David Bortz and Michael Norman Grimshaw discloses a quetiapine therapy that administers a major quetiapine component in an immediate release form and a minor quetiapine component in an extended release, delayed extended release, or delayed pulsed release form (see [0018]-[0020]). For a sleep disorder, the daily dosage of quetiapine is about 50 to 300 mg. Dosages lower than this range may be administered at the beginning of a treatment period (see [0045]). Optionally, the quetiapine is administered together with an additional pharmaceutical agent. The pharmaceutical agent may be any pharmaceutical agent appropriate to the condition (see [0124]). In one embodiment, the quetiapine is administered together with a sleep aid, which may be zolpidem (see [0125] and [0130]). No advantages for zolpidem over other sleep aids are disclosed, and no dosages for zolpidem are disclosed. In fact, zolpidem is mentioned as only one of approximately ninety-four other "additional pharmaceutical agents" that can be used in combination with quetiapine. Thus, this reference in fact makes it more difficult for one skilled in the art to solve the issues with quetiapine than if the reference did not exist, as it would require a huge multitude of experiments to distinguish which of the ninety-four agents would be useful and in what dosage.

Other sleep potions either do not work well, have serious side effects, or both. For example, while over-the-counter medications work on some, they do not work for all, and usually do not continue to work over extended periods. Further, in higher doses, most become a stimulant. Thus, if the user does not fall asleep immediately, the user may take an additional dose and not be able to sleep at all.

For the above reasons, there remains a significant need for a sleep composition and method that is safe and effective, particularly over extended periods, and does not have significant side effects.

SUMMARY OF THE INVENTION

The invention not only provides a composition and method effective in promoting sleep but also does so without the side effects and undesirable consequences of sleep remedies in the prior art. Further, the composition according to the invention is effective at relatively low dosages and remains effective at low dosages over long periods of time.

The invention provides a single sleeping pill comprising a homogeneous combination of two well-known pharmaceutical sleep aids, quetiapine and zolpidem, which have a different effect when taken together than when taken alone. Preferably, the amounts of each of the pharmaceutical sleep aids in the homogeneous combination are lower than the amounts of each individual sleep aid that are required to consistently get seven to eight hours of sleep a night when the pharmaceutical sleep aids are taken alone. A surprising result of a trial of the inventive combination was that the most significant side effects that occurred when the individual sleep aids were taken alone, i.e., an inability to sleep without the sleep aid, the need for increasing dosages, weight gain, and somnolence in the case of quetiapine, did not reoccur when the ingredients were taken together.

The invention also provides a pill comprising: a homogeneous combination of a first compound and a second compound, wherein: the first compound comprises zolpidem and the second compound comprises quetiapine. Preferably, the combination comprises from 1 mg to 10 mg of the first compound combined with from 5 mg to 50 mg of the second compound. Preferably, the combination comprises from 1.5 mg to 9 mg of the first compound. Preferably, the combination comprises from 2 mg to 8 mg of the first compound. Preferably, the combination comprises from 3 mg to 7 mg of the first compound. Preferably, the combination comprises 5 mg of the first compound. Preferably, the combination comprises from 10 mg to 45 mg of the second compound. Preferably, the combination comprises from 15 mg to 35 mg of the second compound. Preferably, the combination comprises from 20 mg to 30 mg of the second compound. Preferably, the combination comprises 25 mg of the second compound.

In another aspect, the invention provides a method of promoting sleep in a human, the method comprising: preparing a homogeneous composition comprising a first compound comprising zolpidem and the second compound comprising quetiapine; and orally or parenterally administering the composition to a human prior to a sleep period. Preferably, the zolpidem and quetiapine are included in the composition only in their immediate release forms.

Preferably, no other pharmaceutical compound is used with the combination of compound I and compound II. It is particularly preferable that no other pharmaceutical that is known to affect the nervous system should be taken with the combination of compound I and compound II. In particular, a 4-acylaminopyridine derivative, an HMG Coenenzyme A Reductase (HMGCR) modulating agent, a melanocortin receptor, an angiotensin modulator, a peroxisome proliferator-activated receptor (PPAR) agent, or any other first neurogenic agent described in the '671 Application, the '165 application, the '105 Application, the '574 Application, and the '291 Application cited above should not be used in the combination according to the invention. Further, the lithium compounds of the Satow Application should be avoided.

It is also preferable that extended release, delayed extended release, or delayed pulsed release forms of the combination according to the invention be avoided, as these could create undesirable side effects.

In yet a further aspect, the invention provides a pill comprising: a composition comprising a first compound and a second compound, wherein: the first compound comprises zolpidem and the second compound consisting essentially of quetiapine in immediate release form. Preferably, the composition consists essentially of the zolpidem and the quetiapine. Preferably, the composition comprises from 1 mg to 10 mg of the zolpidem combined with from 5 mg to 45 mg of the quetiapine. Preferably, the zolpidem and quetiapine are included in the composition only in their immediate release forms.

In a further aspect, the invention provides a pill comprising: a composition comprising from 1 mg to 10 mg of zolpidem and from 5 mg to 45 mg of quetiapine. Preferably, the composition comprises from 1.5 mg to 9 mg of the first compound. Preferably, the composition comprises from 2 mg to 8 mg of the first compound. Preferably, the composition comprises from 3 mg to 7 mg of the first compound. Preferably, the composition comprises 5 mg of the first compound. Preferably, the composition comprises from 10 mg to 45 mg of the second compound. Preferably, the composition comprises from 15 mg to 35 mg of the second compound. Preferably, the composition comprises from 20 mg to 30 mg of the second compound. Preferably, the combination comprises 25 mg of the second compound. Preferably, the zolpidem and quetiapine are included in the composition only in their immediate release forms.

In another aspect, the invention provides a pill comprising: a composition comprising zolpidem and quetiapine, the quetiapine being in immediate release form, the pill and the composition not including a 4-acylaminopyridine derivative, an HMG Coenenzyme A Reductase (HMGCR) modulating agent, a melanocortin receptor, an angiotensin modulator, a peroxisome proliferator-activated receptor (PPAR) agent, lithium, or quetiapine in an extended release, delayed extended release, or delayed pulsed release form.

The invention also provides a method of promoting sleep in a human, the method comprising: preparing a pill consisting of a first compound comprising zolpidem and a second compound comprising quetiapine, the zolpidem and the quetiapine included in the composition in an, amount sufficient to prevent tolerance to and addiction to the zolpidem; preferably, the combination and the amount also prevents tolerance to and the need for increasing dosages of the quetiapine; the composition is orally or parenterally administered to a human prior to a sleep period for a period longer than two months. Preferably, the composition is administered daily for a period longer than four months. More preferably, the composition is administered daily for a period of six months. Most preferably, the composition is administered daily for a period of a year or more. Preferably, the combination also prevents the development of tolerance to the quetiapine. Preferably, the zolpidem and quetiapine are included in the composition only in their immediate release forms.

The invention provides a pill comprising: a composition comprising a first compound and a second compound, wherein: the first compound comprises zolpidem; the second compound comprises quetiapine; and wherein the composition comprises from 1 mg to 10 mg of the zolpidem combined with from 5 mg to 45 mg of the quetiapine.

The invention also provides a pill comprising: a composition comprising zolpidem and quetiapine, the zolpidem and the quetiapine included in the composition in amounts wherein the quetiapine essentially eliminates the side affect of the zolpidem which hinders sleep without using the zolpidem. Preferably, the zolpidem and the quetiapine are included in the composition in amounts wherein the zolpidem essentially eliminates the side effect of the quetiapine which results in weight gain or the side effect that results in somnolence.

In a further aspect, the invention provides a composition comprising essentially zolpidem and quetiapine, the zolpidem included in the composition in an amount less than an amount that leads to tolerance to or addiction to the zolpidem, and the quetiapine included in the composition in an amount less than an amount that leads to tolerance to or addiction to the quetiapine, the quetiapine being in immediate release form, the pill and the composition not including a 4-acylaminopyridine derivative, an HMG Coenenzyme A Reductase (HMGCR) modulating agent, a melanocortin receptor, an angiotensin modulator, a peroxisome proliferator-activated receptor (PPAR) agent, lithium, or quetiapine in an extended release, delayed extended release, or delayed pulsed release form.

In another aspect, the invention provides a method of promoting sleep in a human, the method comprising: preparing a composition consisting of a first compound comprising zolpidem and a second compound comprising quetiapine, the zolpidem included in the composition in an amount less than an amount that leads to tolerance to or addiction to the zolpidem, and the quetiapine included in the composition in an amount less than an amount that leads to tolerance to or addiction to the quetiapine; and orally or parenterally administering the composition essentially daily to a human prior to sleep for a period longer than two months. Preferably, the entire amount of the zolpidem and the quetiapine are provided in the composition only in their immediate release forms.

In yet a further aspect, the invention provides a combination of pills comprising: a first pill comprising a first composition comprising zolpidem and quetiapine; and a second pill comprising a second composition comprising zolpidem and quetiapine; wherein the ratio of the amount of zolpidem in milligrams to the amount of quetiapine in milligrams in the first pill is a first ratio, and the ratio of the amount of zolpidem in milligrams to the amount of quetiapine in milligrams in the second pill is a second ratio different from the first ratio. Preferably, the first ratio differs from the second ratio by 5% or more. Preferably, the first ratio is from 1/50 to 1/5. Preferably, the second ratio is from 1/4 to 2. Preferably, the first ratio is from 1/50 and 1/5 and the second ratio is from 1/4 to 2. Preferably, the invention further includes a third pill comprising zolpidem and quetiapine wherein the ratio of the zolpidem in milligrams to the quetiapine in milligrams in the third pill is between the first ratio and the second ratio.

In still another aspect, the invention provides a method of marketing a sleeping aid, the method comprising: providing a first pill comprising a first composition comprising zolpidem and quetiapine; and providing a second pill comprising a second composition comprising zolpidem and quetiapine; wherein the ratio of the amount of zolpidem in milligrams to the amount of quetiapine in milligrams in the first pill is a first ratio, and the ratio of the amount of zolpidem in milligrams to the amount of quetiapine in milligrams in the second pill is a second ratio different from the first ratio.

A preferred method of administration is in a capsule or equivalent form. Preferably, in the capsule, or other form, the zolpidem is in the form of a finely divided powder, liquid, or other conventional, easily digested form that will be assimilated into the body quickly, while the quetiapine is in the form of a solid pellet or other conventional form that is still considered as immediate release in the art but is digested and assimilated more slowly than a finely divided powder or liquid.

The invention provides for the first time a sleep aid that, when taken prior to going to bed, mimics a normal healthy sleep cycle. In addition, significant side effects that occur when the individual ingredients of the composition are taken alone do not occur. Numerous other advantages and features of the invention will become apparent from the following detailed description.

DETAILED DESCRIPTION OF THE PREFERRED EMBODIMENT

The invention comprises a sleeping aid combination including a compound having the formula:

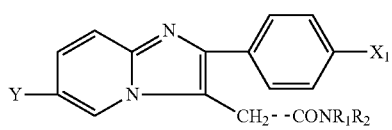

where $X_1$ is a halogen or methyl; Y is hydrogen, a halogen, or methyl; $R_1$ is hydrogen, $C_{1-5 alkyl\ or\ hydroxyl}(C_{1-5\ alkyl})$; and $R_2$ is $C_{1-5alkyl\ or\ hydroxy}(C_{1-5\ alkyl})$ or a pharmaceutically acceptable salt thereof, herein referred to as compound I, in combination with a compound having the formula:

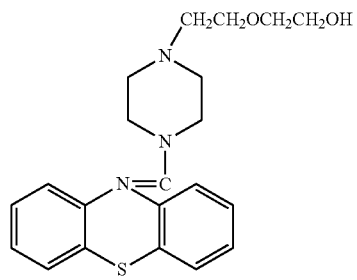

and acid addition salts thereof, herein referred to as compound II.

Compound I is alternatively referred to herein as zolpidem while composition II is alternatively referred to herein as quetiapine. Compound I or zolpidem is sold under a myriad of commercial names, including Adormis, Ambien, Ambien CR, Edluar, Zolpimist, Damixan, Hypnogen, Ivedal, Lioran, Myslee, Nasen, Nytamel, Sanval, Somidem, Stilnoct, Stilnox CR, Sucedal, Zoldem, Zolnod, and Zolpihexal. In this patent application, the terms compound I and zolpidem include all of the above without limitation. According to the Wikipedia entry for zolpidem and an article cited therein, zolpidem has not adequately demonstrated effectiveness in maintaining sleep. See Rosenberg, R. P., *Sleep maintenance insomnia: strengths and weaknesses of current pharmacologic therapies, Ann Clin Psychiatry* 18(1): 49-56 (January-March 2006). It is not unusual for physicians to prescribe 20 mg a night after zolpidem has been used for a year or more, and even that eventually is not able to get the user to sleep.

Compound II is marketed by AstraZeneca as quetiapine and by Orion Pharma as Ketipinor, both as a quetiapine fumarate salt of the compound. The compound is also marketed as Quepin by Specifar ABEE in Athens Greece. See Wikipedia entry for quetiapine. In this patent application, the terms compound II and quetiapine include all of the above without limitation. Compound II is an atypical antipsychotic used in the treatment of schizophrenia and depression and used off-label for a variety of other purposes, including insomnia and anxiety disorders. To treat psychotic symptoms, AstraZeneca recommends using 200-880 milligrams (mg) a day, split into two or three doses per day. For chronic insomnia, 100 mg a night is typically used. The use of quetiapine for insomnia at the above dosage is not recommended as it is an antipsychotic medication designed to treat psychotic symptoms, and there is a danger of neurological and cognitive side effects including possible damage to brain regions controlling wake-sleep cycles. See Breggin, P. R. (1990) *Brain damage, dementia and persistent cognitive dysfunction associated with neuroleptic drugs. Evidence, etiology, implications, Journal of Mind and Behavior,* 11, 425 64. However, the preferred dosages of quetiapine according to the invention are far below the dosages generally prescribed for either antipsychotic usages or insomnia and there is no evidence of any such side effects at such low dosages.

Compound I is disclosed in detail in U.S. Pat. No. 4,382,938 issued May 10, 1983 to Jean-Pierre Kaplan and Pascal George, which patent is incorporated herein by reference to the same extent as completely disclosed herein. Compound II is disclosed in U.S. Pat. No. 4,879,288 issued Nov. 7, 1989 to Edward J. Warawa and Bernard M. Migler, which patent is incorporated herein by reference to the same extent as though fully disclosed herein.

The composition comprising compound I and compound II for the first time provides a sleeping aid that reproduces the normal sleep pattern of a healthy human being. That is, it quickly induces sleep, keeps the user asleep for a normal night's sleep, allows the user to awaken at a variable time without after affects, permits the user to take naps during the day, if that is what the user likes to do, and, as of yet, has no significant side effects. In particular, the somnolence often associated with quetiapine and the addiction associated with zolpidem do not occur at the preferred dosages of the composition.

The invention comprises the composition comprising a combination of compound I and compound II in a sleeping aid pill. The term "pill" herein means includes a tablet or capsule, or any other form in which medicine is conventionally ingested. While each compound has been used before, by itself, and, in fact is well-known as a sleeping aid, they have never before been provided in combination at the dosages disclosed. In particular, they have never been provided at the preferred dosages according to the invention. As discussed in detail below, this composition has properties not found in the individual compounds used alone. Further, in the preferred composition according to the invention, the amounts of each compound are substantially less than the amounts of each compound generally prescribed as sleeping aids.

The preferred composition comprises from 1 mg to 10 mg of compound I combined with from 5 to 50 mg of compound II. Preferably, the composition comprises from 1.5 mg to 9 mg of compound I, more preferably the composition comprises from 2 mg to 8 mg of compound I, and most preferably the composition comprises from to 3 mg to 7 mg of compound I. In the optimum formulation, the composition comprises 5 mg of compound I. Preferably, the composition comprises from 10 mg to 45 mg of compound II, more preferably the composition comprises from 15 mg to 35 mg of compound II, and most preferably the composition comprises from to 20 mg to 30 mg of compound II. In the optimum formulation, the composition comprises 25 mg of compound II. Even the largest preferred composition includes substantially less of each compound than the preferred dosages of the compounds when used alone after tolerance has been developed.

It is preferable that no other pharmaceutical compound is used with the combination of compound I and compound II. It is particularly preferably that no other pharmaceutical that is know to affect the nervous system should be taken with combination of compound I and compound II. In particular, a 4-acylaminopyridine derivative, an HMG Coenenzyme A Reductase (HMGCR) modulating agent, a melanocortin receptor, an angiotensin modulator, a peroxisome proliferator-activated receptor (PPAR) agent, or any other first neurogenic agent described in the '671 Application, the '165 application, the '105 Application, the '574 Application, and the '291 Application cited above should not be used with the combination compound I and compound II according to the invention. As will be shown below, there is an interaction, a balance between compound I and compound II that may be upset by any such agent. In addition, a 4-acylaminopyridine derivative, an HMG Coenenzyme A Reductase (HMGCR) modulating agent, a melanocortin receptor, an angiotensin modulator, a peroxisome proliferator-activated receptor (PPAR) agent and any other first neurogenic agent described in the '671 Application, the '165 application, the '105 Application, the '574 Application, and the '291 Application may create undesirable side effects. For example, angiotensin modulators constrict the blood vessels which raise the blood pressure. This is highly undesirable in persons already predisposed to effects of high blood pressure. In particular, sleep disorders often are associated with older persons who may already be having some sexual dysfunction, and blood vessel constriction further aggravates this condition. Indeed, there are so many agents listed in the BrainCells applications that some of them are bound to create complications with the sleep aid described herein. Further the, lithium compounds of the Satow Application should be avoided as lithium treatment is known to have severe side effects, including death.

A feature of the invention is that extended release, delayed extended release or delayed pulsed release forms of the combination according to the invention are unnecessary as the combination according to the invention already permits normal sleep. While the use of extended release would not be completely unwarranted, particularly if the release of the zolpidem is six hours or less and the release of the Quetiapine is four hours or less, in fact, extended release, delayed extended release or delayed pulsed release forms are better to be avoided as these extend the time that the compound I and compound II are in the body and likely will result in the side effects associated with the individual compounds returning. Preferably, the combination is provided in a normal tablet form. Another preferred method of administration is in a capsule. Preferably, in the capsule, or other form, the zolpidem is in the form of a finely divided powder, liquid or other conventional easily digested form that will be assimilated into the body quickly, i.e., in a half-hour or less and more preferably in fifteen minutes or less, while the quetiapine is in the form of a solid pellet or other conventional form that is digested and assimilated more slowly, i.e., in a half-hour or more and more preferably in an hour or more. That is, in the preferred embodiment, the zolpidem is in a release form that is faster than the quetiapine and the quetiapine is in a release form that is slower than the release form of the zolpidem.

A feature of the invention is that the composition according to the invention is significantly more effective than the compounds used alone. Another feature is that common side effects of the compounds when used alone disappear when the compounds are used together. A further feature of the invention is that it does not appear to be addictive, that is, larger dosages are not required after extended use. A further feature of the invention is that the user returns to normal, healthy sleep patterns. That is, the user falls asleep quickly upon retiring, and can sleep a full seven to eight hours. However, if due to a need to arise sooner, the user can wake to an alarm as a normal sleeper, or if the user has been deprived of a normal night's sleep for a period, the user can sleep up to ten hours or more and make up sleep just as a healthy young person does. Further, if a user's normal sleep pattern is to sleep less at night and take a nap during the day, the user can do this without any issues. Another feature of the invention is, as of the current state of testing, there does not appear to be any adverse side effects.

The invention was discovered when the inventor accidently took a small amount of compound I together with a small amount of compound II. The inventor had been prescribed compound I by his physician but the amount he needed kept increasing. The physician then prescribed compound II, and told the inventor that he could use up to 100 mg, but to try to keep the dosages lower. One night the inventor took 25 mg of compound II to see if he, could get by on a minimum dosage. After tossing for an hour, the inventor decided to take a further small dose of compound II, and went to his medicine cabinet. He still had some small pieces of compound I in a bottle in the medicine cabinet, which were about the same size as a portion amounting to less than half of one of the compound II pills. The inventor mistakenly took a small piece of compound I, immediately fell asleep and slept for six hours, got up to empty his bladder (the inventor is seventy-one years old) and went back to bed and slept for another two hours. He was completely surprised as, for more than three years, he had not been able to go back to sleep after waking except by taking additional sleep aid. When he got up in the morning, he found the compound I container on the bathroom sink and thus discovered that he had taken compound I instead of compound II.

In the interests of full disclosure, details of the inventor's sleep background and the effects of the inventive compound on the inventor will be disclosed so that one skilled in the art can better evaluate the compound and its use. The inventor had a healthy sleep pattern until he was about in his late 50's to early 60's. That is, the inventor could usually fall asleep at night within about fifteen minutes of going to bed. He would sleep about eight hours and get up rested. At times, when he had formed the habit of getting up at the same time each morning, he would awake at the proper time without an alarm. If he did not have the time to sleep eight hours, he could get up with an alarm and still function well during the day. He could also go without sleep for extended periods or function with periods of sleep less than eight hours on sequential nights, and then make up for it with a night of sleep that was longer than eight hours. His sleep was normal, with dreams, REM sleep, etc. At times, particularly after the age of fifty, he would awake during the night to empty his bladder, then quickly return to sleep. He regular drank caffeinated drinks such as cola drinks without affecting his sleep.

After about 60, particularly at times of stress, he would take over-the-counter sleep medicines. However, these were only sporadically effective. At about the age of 62, insomnia became an issue, leading to lessened resistance to disease, even to a bout of pneumonia, and lessened ability to concentrate and work. Over-the-counter medicines sometimes created issues when he took too much and they turned into stimulants. However, on weekends and when stress levels became less, he was able to get back to better sleep patterns. In addition, he became very sensitive to caffeine, and any caffeine during the day would prevent sleep.

At about 66, insomnia became nearly dehabilitating. He not only had difficulty going to sleep, but by that age he was getting up nearly every night to empty his bladder and had difficulty falling back to sleep. He became desperate, trying a wide variety of over-the-counter remedies, diets and sleep methods. The one thing that kept him going was that he was able to take a nap of an hour or longer after lunch. His physician performed tests, such as testing for sleep apnea, with no positive results. Finally, he requested—perhaps demanded—a prescription medicine from his physician. His doctor prescribed Ambien, and later, the generic form of Ambien, zolpidem. At first this was like a miracle, though it kept him to sleep only for about four hours. He developed a routine of sleeping four hours, getting up to empty his bladder, then taking another dose of Ambien, and, later, when generics became available, zolpidem. He started with a nightly dose of about 5 mg, but the amount needed quickly increased to 10 mg, and over a two year period, the amount required to sleep increased to 20 mg. The inventor would break his Zolpidem tablets into small pieces so he could take it in multiple doses during the night, and, in particular, if he really needed extra sleep at five or six in the morning, he would take a small piece of zolpidem to try to get the little extra sleep. This did not always work as a small piece was often no longer enough to get him to sleep. Also, his sleep did not seem normal, as he did not have dreams.

What was worse, he became unable to sleep without zolpidem. Afternoon naps were not possible. Making up sleep over the weekend became impossible without taking zolpidem. Naps were not possible. It became impossible to get back to sleep after waking without taking additional zolpidem. His physician had him try quetiapine in the form of Seroquel. He started with 75 mg while he was breaking the zolpidem habit, and reduced it gradually to 50 mg. This did get him off the zolpidem, but had other problems, such as leaving him drowsy, especially in the mornings. He tried to reduce it to 25 mg, but he found that while 25 mg did not leave him drowsy after getting up, it usually kept him sleeping only about 5 or six hours.

Even at 25 mg, there were problems. He had to anticipate when he was going to sleep and take the quetiapine an hour to an hour and a half before going to bed. If he took the quetiapine and unexpected events, such as his wife wanting to talk for a while, or a teenager staying up too late, kept him from sleeping at the designated time, it sometimes was difficult to get to sleep. One way to handle the fact that 25 mg only worked for about six hours of sleep, was that when he got up to urinate, he would take additional quetiapine. In particular, he took additional quetiapine on the weekends to get extra sleep. However, whenever he took the additional quetiapine to get the extra sleep, this left him a bit groggy during the early part of the day. But, except for the need to take more of the quetiapine to sleep longer, the average amount he needed to get to sleep did not increase as it had for zolpidem. Also, he could again nap in the afternoon, and dreams returned. However, he gained weight, going from a range of about 170-174 pounds he had held to for ten years, to 184 pounds.

Then, came the night when the inventor accidently took a small piece of zolpidem, about 3 mg, shortly after he had taken a 25 mg dose of quetiapine. As mentioned above, he immediately went to sleep and slept a full eight hours. When this worked well, he tried it again the next few nights, taking the 25 mg of quetiapine with 3-5 mg of zolpidem at the same time just before he was ready to sleep. He has done this now for over five months with results that, to a person who had not had a solid nights sleep for about ten years, truly amazing. He is back to the sleep patterns he had as a young man. He usually falls asleep at night within about fifteen minutes of taking the medication. He sleeps eight hours and gets up rested. When he gets into a pattern of getting up at same time each morning, he awakes at the proper time without an alarm. If he must get up early for travel or some other reason and cannot sleep eight hours, he can get up with an alarm and still function well during the day. If he goes for a period when he does not get a full eight hours each night, he can make it up on the weekends. He can get up at almost any time during the night, and go back to sleep. Usually, the time he gets up to empty his bladder is after about six hours instead of the four or even three hours as it was with zolpidem alone, though there are many nights he has slept eight hours straight. Naps are easily taken, but are not as necessary as the user usually gets eight hours sleep each night. Fairly often, he has slept a full eight hours without the usual getting up to urinate. His sleep is normal, with dreams, REM sleep, etc. Weight has dropped slowly to 177 pounds, and appears to be going toward the usual 170-174. Also, strangely, he can drink caffeinated drinks such as cola drinks without affecting his sleep. This is surprisingly enjoyable for one who had not had coffee or caffeinated cola for over twenty years.

The amounts of the two compounds have been varied as indicated above with all amounts within the ranges indicated appearing to work, with the preferred amounts for the present user being as described. However, it may be that the preferred amounts will be different for different users. It is possible that the amount of quetiapine can be additionally decreased, though this has not yet been done for an extended period due to the fact that the prescribed pill is 25 mg and is difficult to cut.

It is evident that something more than just the combined individual effects of the two sleeping compounds. The disappearance of the principal side effects, i.e., the inability to sleep without the drug which resulted from zolpidem and the weight gain and somnolence of quetiapine, is remarkable as the same dosage of zolpidem alone prevents naps. What is even more surprising, on weeks that the user has missed a lot of sleep because of travel, children, etc., the user has been able to sleep in on Sunday morning until he was refreshed, getting about ten hours sleep with no additional medication. The amount of sleep depends on how tired the user is, not on how much sleep aid the user has taken. The amount of zolpidem or quetiapine required has not increased over time. Well being and non-grogginess in the early morning is significantly better than when taking quetiapine alone or zolpidem alone, yet when the user wants to sleep or nap, that is no problem. For the first time in almost ten years, the user is sleeping normally, and as a result is becoming more healthy and active. The inventor's sleep is normal, with dreams, REM sleep, etc. The resulting physiological and psychological well being can only be appreciated by those who have had a long struggle with insomnia.

It is known that quetiapine acts differently at low dosages, i.e., less than 25 mg, then at high dosages, i.e., at dosages over 200 mg. However, the dosage being taken as described above was at the low end both when taken alone and taken in combination with the zolpidem. What is completely unexpected is the effect on sleep beyond about six hours. After about six hours, the user can return to sleep for a few more hours, if desired, or get up without an extended period of drowsiness— the difference between getting up after six hours sleep and getting up after eight hours sleep being similar to the normal human reaction to not getting a full night's sleep and the refreshed feeling after eight hours sleep. It is evident that both zolpidem and quetiapine remain in the body or at least have effects that remain in the body long after their effectiveness in assisting sleep has dissipated. It is possible that the lingering effects of the two drugs either cancel each other out or interact in a positive manner.

It is known to manufacture and market medications in various concentrations. For example, The composition according to the invention may be manufactured and marketed in a low dosage form of between 1 to 3 mg of zolpidem and 5 to 20 mg of quetiapine, an intermediate dosage form of from 3 to 7 mg of zolpidem and 15-30 mg of quetiapine, and a high dosage form of from 7 to 10 mg of zolpidem and 30-50 mg of quetiapine. However, after using the composition for more than a year and confidential discussions with physicians, it has become evident that manufacturing and marketing the composition with different ratios of zolpidem and quetiapine would be useful. For example, manufacturing and marketing in a low zolpidem/quetiapine ratio and a high zolpidem/quetiapine ration would be useful. The forgoing in combination with a mid zolpidem/quetiapine ratio would also be useful. For example, the low ratio composition would be 1-5 mg of zolpidem combined with 25-50 mg of quetiapine and the high ratio composition would be 5-10 mg of zolpidem combined with 5-20 mg of quetiapine. A mid ratio composition may be 3-7 mg of zolpidem combined with 20-30 mg of quetiapine. Preferably the low ratio composition would be 3-4 mg of zolpidem and 30-50 mg of quetiapine, the mid ratio composition would be 4-6 mg of zolpidem and 20-30 mg of quetiapine, and the high ratio composition would be 7-10 mg of zolpidem and 5-20 mg of quetiapine. More preferably the low ration combination would be 3 mg of zolpidem combined with 50 mg of quetiapine, the mid ration combination would be 5 mg of zolpidem combined with 25 mg of quetiapine, and the high ration combination would be 10 mg of zolpidem combined with 15 mg of quetiapine. Other combinations may be possible also. The availability of the low, mid and high ration combinations would be useful for the physician in prescribing the medication. For example, the physician my prescribe a low ration combination for a patient who has little trouble in getting to sleep but has trouble staying asleep, and a high ratio combination for a patient who has trouble getting to sleep but not so much trouble staying asleep. For therapy to get a patient off of zolpidem dependence, the physician may start with a high ratio combination and then switch to a mid ration combination, and then to a low ration combination. The mid ratio combination would be particularly useful for getting a patient who has had no previous experience with either zolpidem of quetiapine started on the medication. The patient would also find it useful to have the medication available in several ratios. The patient, for example, may use the low ration combination on a night that he or she is quite tired and expects little trouble falling asleep but would like to sleep in on the next day, for example a Friday night. Or the patient may use the high ratio combination on a night after a troubling day when the patient knows he or she will have lots of thoughts going through his or her head making getting to sleep difficult, but needs to be up bright and early the next morning to tackle the day's problems. The mid ration combination would be used otherwise. The inventor has found that varying the ratio of the combination depending on his needs and expectations each night has been useful in getting the desired amount of sleep each night and also in preventing tolerance to the medication from occurring. Summarizing, the invention provides a first pill comprising a first composition comprising zolpidem and quetiapine; and a second pill comprising a second composition comprising zolpidem and quetiapine; wherein the ratio of the amount of zolpidem in milligrams to the amount of quetiapine in milligrams in the first pill is a first ratio and the ratio of the amount of zolpidem in milligrams to the amount of quetiapine in milligrams in second pill is a second ratio different from the first ratio. Preferably, the first ratio differs from the second ratio by 5% or more. Preferably, the first ratio is from 1/50 to 1/5. Preferably, the second ratio is from 1/4 to 2. Preferably, the first ratio is from 1/50 and 1/5 and the second ratio is from 1/4 to 2. Preferably, the invention further includes a third pill comprising zolpidem and quetiapine where the ratio of the zolpidem in milligrams to the quetiapine in milligrams in the third pill is between the first ratio and the second ratio. With the present disclosure and a little experience in using the inventive combination, those skilled in the art will be able to create other combinations, ratios, and uses of the composition ratios.

There has been described novels composition for assisting a human in falling asleep and staying asleep for a normal period as well as novel methods of applying the compositions. It should be understood that the specific formulations and methods described herein are exemplary and should not be construed to limit the invention, which will be described in the claims below. Further, it is evident that those skilled in the art may now make numerous uses and modifications of the specific embodiments described without departing from the inventive concepts. As one example, Equivalent compositions and processes may be substituted for the various compositions and processes described; the subprocesses of the inventive method may, in some instances, be performed in a different order; or a variety of different substances may be used with the composition according to the invention. Consequently, the invention is to be construed as embracing each and every novel feature and novel combination of features present in and/or possessed by the compositions and methods described herein.

I claim:

1. A pill comprising:
   a composition comprising a first compound and a second compound, wherein:
   said first compound comprises zolpidem;
   said second compound comprises quetiapine; and
   wherein said composition comprises from 1 mg to 10 mg of said zolpidem combined with from 5 to 45 mg of said quetiapine.

2. A pill as in claim 1 wherein said composition consists essentially of said zolpidem and said quetiapine.

3. A pill as in claim 2 wherein said composition comprises less than 5 mg of said zolpidem.

4. A pill as in claim 2 wherein said composition comprises from 10 mg to 45 mg of said quetiapine.

5. A pill as in claim 2 wherein said composition comprises less than 25 mg of said quetiapine.

6. A pill comprising: a composition comprising zolpidem and quetiapine, said zolpidem and said quetiapine included in said composition in amounts wherein said quetiapine essentially eliminates the side effect of said zolpidem which hinders sleep without using said zolpidem.

7. A pill as in claim 6 wherein said zolpidem and said quetiapine are included in said composition in amounts wherein said zolpidem essentially eliminates the side effect of said quetiapine which results in weight gain or the side effect of quetiapine that results in somnolence.

8. A pill as in claim 1 wherein said zolpidem and said quetiapine are included in said composition in an amount sufficient to prevent tolerance to or addiction to said zolpidem.

9. A pill comprising:
   a composition comprising:
      zolpidem, said zolpidem included in said composition in an amount in which, when taken without quetiapine, it has an adverse effect in which the human body develops tolerance for the zolpidem, and larger and larger dosages are required for it to remain effective; and
      quetiapine, said quetiapine included in said composition in an amount wherein said quetiapine essentially eliminates said adverse effect of said zolpidem in which the human body develops tolerance for the zolpidem.

10. A pill comprising:
    a composition comprising:
       quetiapine, said quetiapine included in said composition in an amount in which, when taken without zolpidem, it has a side effect of somnolence (drowsiness); and zolpidem, wherein said zolpidem is included in said composition in an amount which essentially eliminates said side effect of said quetiapine which results in somnolence.

* * * * *